United States Patent [19]
Custer et al.

[11] Patent Number: 6,068,775
[45] Date of Patent: May 30, 2000

[54] REMOVAL OF AGENT FROM CELL SUSPENSION

[75] Inventors: Linda M. Custer, Marlborough; Shawn P. Cain, North Chelmsford; Barbara A. Chandler, Lexington, all of Mass.

[73] Assignee: Circe Biomedical, Inc., Lexington, Mass.

[21] Appl. No.: 09/059,275

[22] Filed: Apr. 13, 1998

[51] Int. Cl.[7] .......................... B01D 61/14; B01D 63/02; C12N 1/04; C12N 1/12
[52] U.S. Cl. ........................ 210/638; 210/638; 210/650; 210/651; 210/500.23; 435/1.3; 435/260; 435/297.4; 435/400
[58] Field of Search .................. 210/500.23, 638, 210/644, 645, 650, 651, 321.79, 321.8, 321.88, 321.89; 435/297.1, 297.4, 1, 3, 260, 400, 297.2; 600/35

[56] References Cited

U.S. PATENT DOCUMENTS

| | | | |
|---|---|---|---|
| 3,874,851 | 4/1975 | Wilkins et al. | |
| 4,212,742 | 7/1980 | Solomon et al. | 210/247 |
| 4,306,556 | 12/1981 | Zelman | 128/272 |
| 4,442,206 | 4/1984 | Michaels et al. | 435/68 |
| 4,464,337 | 8/1984 | Zelman | 422/41 |
| 4,810,394 | 3/1989 | Masuda | 210/767 |
| 4,980,054 | 12/1990 | Lavender | 210/90 |
| 5,071,741 | 12/1991 | Brockbank | 435/1 |
| 5,261,870 | 11/1993 | Hammerstedt et al. | 600/35 |
| 5,456,835 | 10/1995 | Castino et al. | 210/645 |
| 5,510,257 | 4/1996 | Sirkar et al. | 435/182 |
| 5,595,866 | 1/1997 | Critser et al. | 435/2 |
| 5,595,909 | 1/1997 | Hu et al. | 435/297.4 |
| 5,605,835 | 2/1997 | Hu et al. | 435/297.4 |
| 5,622,857 | 4/1997 | Goffe | 435/297.4 |
| 5,776,769 | 7/1998 | Crister et al. | 435/297.2 |

FOREIGN PATENT DOCUMENTS

| | | |
|---|---|---|
| 0 315 420 A2 | 5/1989 | European Pat. Off. |
| WO 95/32624 | 12/1995 | WIPO. |
| WO 96/09876 | 4/1996 | WIPO. |
| WO 96/30492 | 10/1996 | WIPO. |
| WO 96/39817 | 12/1996 | WIPO. |

*Primary Examiner*—Joseph W. Drodge
*Attorney, Agent, or Firm*—Fish & Richardson P.C.

[57] ABSTRACT

The invention relates to a method of removing an agent from a suspension of cells using a semi-permeable membrane. In one aspect of the invention, the cells are used to bioprocess a biological fluid after removal of the agent.

24 Claims, 3 Drawing Sheets

REMOVAL OF AGENT FROM CELL SUSPENSION

BACKGROUND OF THE INVENTION

A bioprocessing system typically includes a bioreactor containing cells that process a fluid. For example, a bioreactor may contain porcine hepatocyte cells to remove toxins from the plasma of a human patient with liver failure.

Prior to their use in a bioreactor, cells can be stored a prolonged period of time in extreme cold in the presence of a cryoprotectant, such as dimethyl sulfoxide (DMSO). Upon thawing cells, removal of the cryoprotectant is desirable or essential prior to their use in a bioreactor. Such an agent is typically removed by centrifuging the cells, followed by washing them with a medium lacking the agent.

SUMMARY OF THE INVENTION

In general, the invention features a method for removing an undesirable agent from a suspension containing cells using a semipermeable membrane.

Included in the invention is a method for bioprocessing a fluid. The method includes the steps of (a) adding a suspension containing cells and an undesirable agent to an enclosure, the enclosure defined in part by a semipermeable membrane which is permeable to the agent but not to the cells; (b) passing a buffer into the enclosure until the agent has been removed from the suspension while the cells remain in the enclosure; and (c) introducing the fluid into the enclosure for bioprocessing by the cells in the enclosure.

In addition to being defined in part by the membrane, the remaining part of the enclosure is defined by a surface impermeable to both the agent and fluid.

In one embodiment, the enclosure is defined in part by the outside surfaces of a multiplicity of bundled hollow fibers made of a semipermeable membrane. In another embodiment, the enclosure is defined largely by the inside surfaces of a multiplicity of such hollow fibers which are bundled together.

Fluids suitable for subsequent bioprocessing include, e.g., plasma, serum, blood, or cell culture media. Also suitable are bioactive fluids such as, e.g., effluent waste streams, which contain substances which can be bioprocessed by certain plant, bacterial, or fungal cells. Because both removal of the agent and bioprocessing take place in the same enclosure in which the suspension of cells is placed for removing the agent, no loss or injury to cells occurs as a result of transfer to a bioprocessing device occurs.

Also included in the invention is a method for removing an undesirable agent from a suspension of cells. The method includes the steps of (a) adding the suspension to a enclosure defined in part by the surfaces of a multiplicity of bundled hollow fibers made of a semipermeable membrane which is permeable to the agent but not to the cells; and (b) passing a buffer into the hollow fiber until the agent has been removed from the suspension through the semi-permeable membrane, while the cells remain in the hollow fiber.

The above-described methods can be used to remove an agent or agents from a suspension of cells, e.g., a preservative, a cryoprotectant such as DMSO or glycerol, or an antibiotic such as gentamicin. In addition, the methods can be used on any cell type, for example, plant, bacterial, fungal, and animal cells, e.g., mammalian cells such as hepatocytes.

As used herein, an "undesirable agent" is any substance whose removal from the suspension is desired, e.g., a substance whose presence in a patient can be harmful to the patient or a substance that impairs the metabolism or viability of cells in the suspension.

The suspension of cells may contain a biomatrix, e.g., a cross-linked dextran bead, to which the cells may attach. The biomatrix, which increases the viability and metabolic activity of cells that are anchorage-dependent, can be added before or after the suspension of cells has been added to the membrane.

The above-described methods have advantages not seen in other systems for removing agents from cells. Cell loss and damage occurring during centrifugation and washing is avoided. Other advantages and features of the invention will be apparent from the following description and from the claims.

DETAILED DESCRIPTION

The invention relates generally to a method of removing an agent from a suspension of cells through a semipermeable membrane. After removal of the agent, the cells may be further used to bioprocess a fluid.

Figure 1:
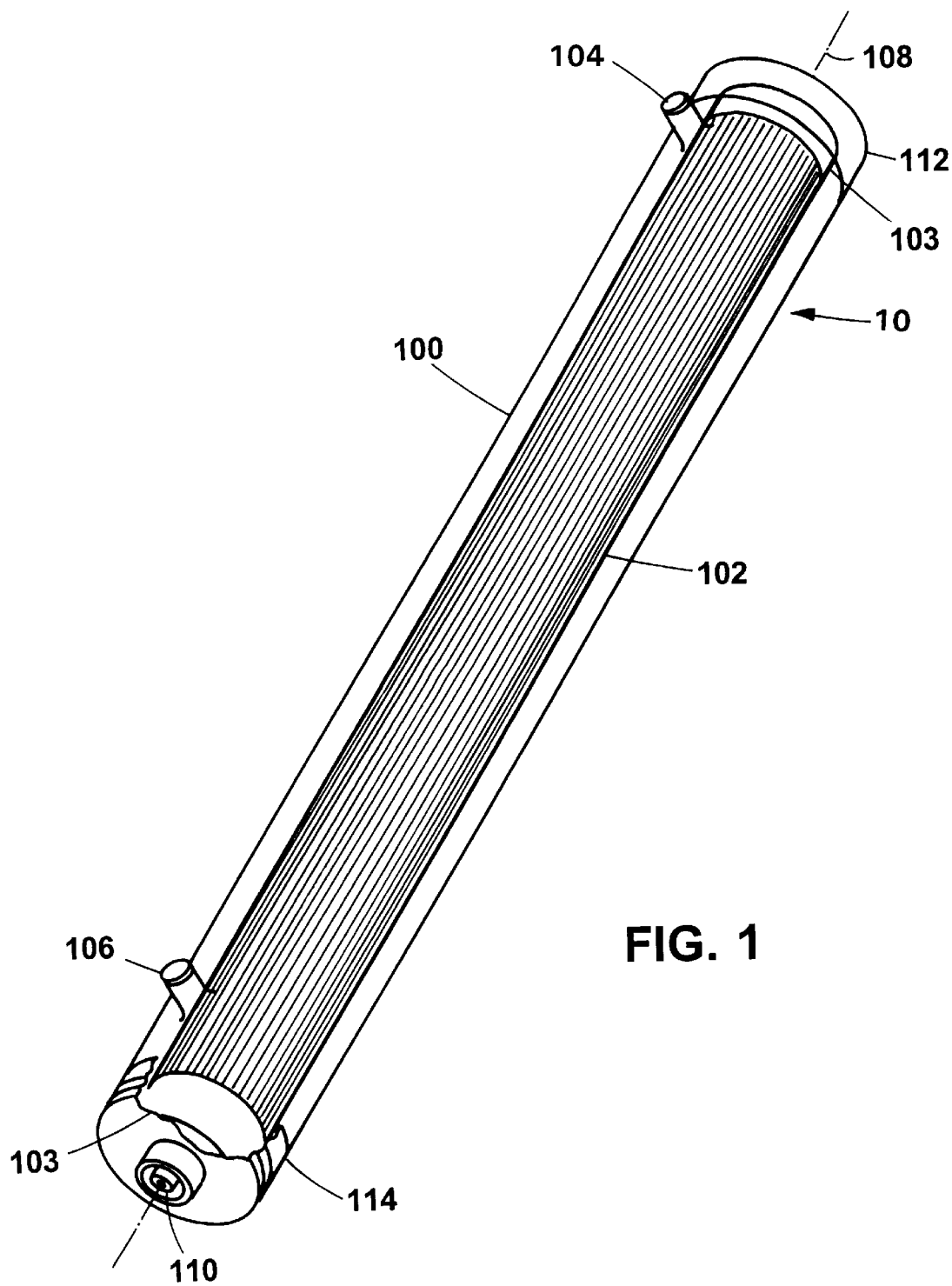
FIG. 1 is a diagrammatic view of a cell encapsulation device having enclosures defined in part by the outside surfaces of hollow fiber semi-permeable membranes.

A cell encapsulation device 10 suitable for use in the methods of the invention is illustrated in FIG. 1. The cell encapsulation device 10 for separating an agent from a suspension of cells includes a housing 100 and has in its interior a multiplicity of hollow fibers made of semipermeable membranes 102. At regions near each end of the cell encapsulation device 10, the spaces between the hollow fibers are a filled with a liquid-impermeable potting material 103, e.g., epoxy or polycarbonate, which holds the hollow fiber membranes in place and occupies an entire cross-section of the cell-encapsulation device 10. The potting material 103 is disposed medially within the cell encapsulation device 10 with respect to the ends of the hollow fibers so that the ends of the hollow fibers are between the potting material and the ends of the cell encapsulation device 10. Thus, an enclosure is formed by the inside surface of the housing 100, the outside surfaces of the hollow fiber membranes 102, and the potting material 103 near each end of the cell encapsulation device 10. The enclosure is shown in FIG. 2C as 202. This region of the cell encapsulation device 10 constituting the enclosure is alternatively referred to as the shell space, or extracapillary space, of the device.

The housing 100 can be made of any suitable biocompatible material, e.g., a plastic such as polystyrene acrylonitrile. The housing 100 may optionally include endcaps 112 and 114 made of a second plastic, e.g., polycarbonate. The membranes 102 have a pore size such that the membrane completely retains the cell component, e,.g., hepatocytes, while allowing passage of the agent to be removed, e.g., a cryoprotectant, and a fluid subsequently added, which contains substances, e.g., toxins, to be bioprocessed. The membranes 102 can be made of any substance that retains its biocompatibility and pore size properties when in contact with the agent and other solution components. Membrane materials include, e.g., polythylene, polypropylene, polycarbonate, teflon, cellulosics such as cellulose acetate, polysulfone, polyether sulfone, polyvinyl alcohol, or polyacrylonitrile.

Referring again to the diagram of FIG. 1, the housing 100 has two laterally disposed ports 104 and 106 for introducing the cells and a wash buffer to the enclosure. Also shown are longitudinal inlet port 108 and longitudinal outlet port 110 at each end of the housing 100. Both longitudinal ports are in communication with the lumen of the hollow fibers. Thus, longitudinal ports 108 and 110 allow for the lumen of the hollow fiber membranes to be connected to a system which provides a fluid such as plasma or blood for bioprocessing. Because the membranes of the hollow fibers are permeable to the fluid, cells in the enclosure can bioprocess the fluid introduced through the lumen. The fluid, which enters through longitudinal inlet port 108, is bioprocessed by the cells contained within the enclosure and can return through the membranes of the hollow fibers to the lumen and exit the cell encapsulation device 10 through longitudinal outlet port 110.

To assemble the cell encapsulation device 10, hollow fibers are cut to a length matching that of the cell encapsulation device 10 and placed inside the housing 100 in a relatively dense, or bundled, packing. The potting material can be introduced into lateral ports 104 and 106, and then directed to regions near the ends of the housing 100, e.g., by centrifuging the cell encapsulation device.

Figure 2A:
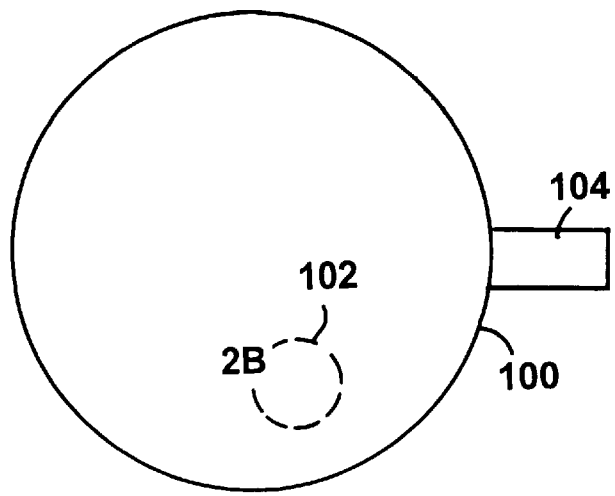
FIGS. 2A–2C are cross-sectional views of the device shown in FIG. 1.
Figure 2B:
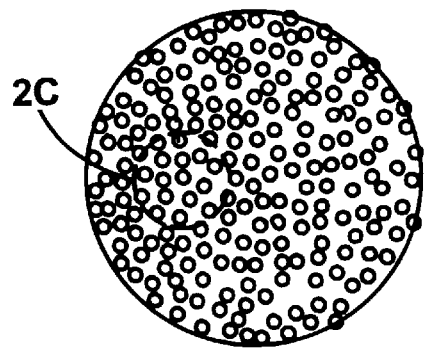
Figure 2C:
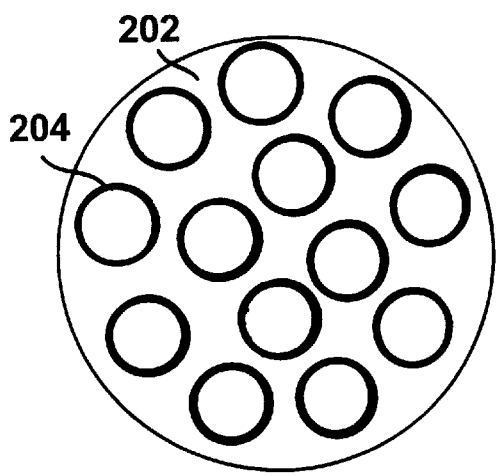

The way in which the hollow fibers in the cell encapsulation device 10 are arranged to produce an enclosure 202 and lumen 204 is shown in FIGS. 2A, 2B, and 2C. The hollow fibers 102 of the cell encapsulation device 10 extend longitudinally within the device, in a direction roughly parallel with the walls of the housing. In the embodiment shown in FIGS. 2A–2C, the hollow fibers are approximately 270 μm inner diameter ×310 μm outer diameter ×450 mm length, with a total of about 4300 hollow fibers in one device. The pore sizes in the membranes of the hollow fibers shown in FIGS. 2A–C are about 0.15 μm.

FIG. 2A is a cross-sectional slice through the a cell encapsulation device 10 showing the housing 100 and about 4300 hollow fibers 102. Also shown in FIG. 2A is a port 104 through which cells can be introduced into the enclosure. FIGS. 2B and 2C are serial expansions of regions containing and surrounding individual porous fibers. FIG. 2C shows the enclosure 202 and the lumen 204 of the hollow fibers.

A process for removing an agent from cells and then using the cells to bioprocess a fluid is summarized in the following flow diagram:

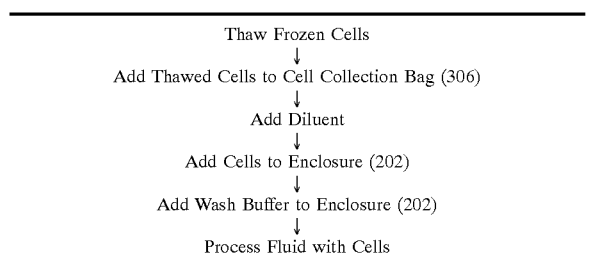

Well in advance of their use of bioprocessing cells, many types of cells, including porcine hepatocytes, are placed within a cell bag 300 with a cryoprotectant such as DMSO, frozen, and stored in a cryostorage freezer. At the time of use, the cells are thawed, after which the cryoprotectant is no longer needed and whose continued presence is no longer desirable.

The manner of thawing is not critical so long as it results in a sufficiently high number of cells that are viable for subsequent handling steps. For porcine hepatocytes, it is desirable to thaw the cell bags 300 by placing them in a water bath at 37° C. to 42° C. for around 2 minutes. This method of cell thawing is described in detail in U.S. application Ser. No. 08/719,769 or corresponding European Patent Application Number 97307459.4 (Publication Number 0834252).

Figure 3:
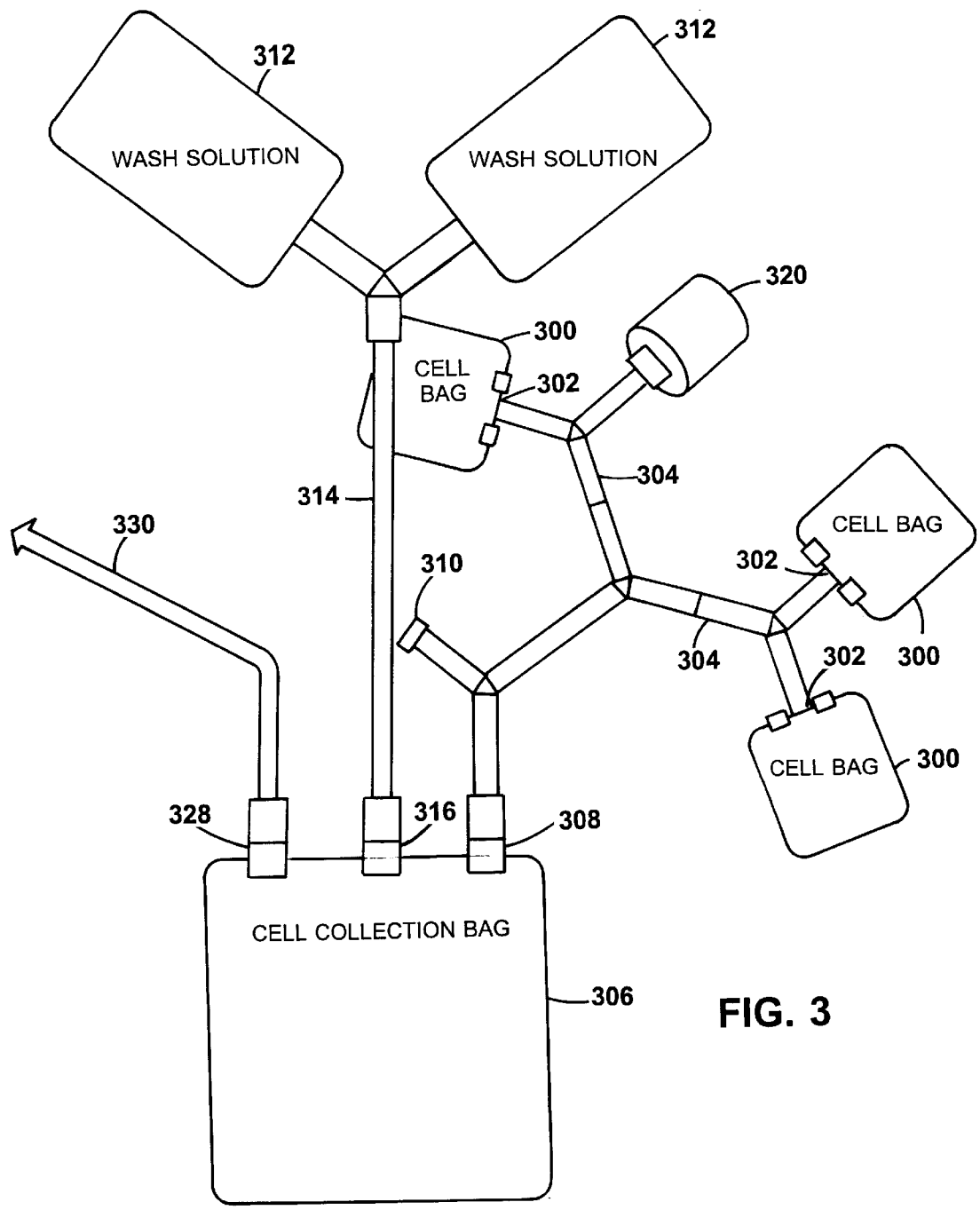
FIG. 3 is a diagrammatic view of a system for adding cells, diluent and microcarriers to a cell collection bag.

Each cell bag 300 has a port 302 which is attached to a conduit 304. As can be seen in FIG. 3, the conduit may be connected to several cell bags 300, (e.g., about 1 to 6 bags), depending on the number of cells needed for the desired application.

The thawed cells are introduced through conduit 304 into a cell collection bag 306 via an inlet port 308. Cells can be delivered into the cell collection bag 306 by simply allowing them to drain into the bag by gravity, or by applying gentle pressure, for example, by using a pressure cuff, a syringe pump, manual pressure, or pneumatic valve system. As will be explained in more detail below, the cell collection bag 306 can be subsequently used to introduce cells into the cell encapsulation device 10 via port 328, which is connected to a conduit 330.

Conduit 304 may contain a port 310 for removing aliquots of cells, for determining cell number and the metabolic activity of the cells.

The thawed suspension of cells may optionally be diluted with an osmotically compatible diluent in the cell collection bag 306. Osmotically compatible diluent solutions include, for example, saline, phosphate-buffered saline (PBS), or lactated Ringer's solution. Diluents are introduced from one or more wash solution bags 312 through a conduit 314 into the cell collection bag 306 via the port 316. Alternatively, diluent solution can also be added directly to the cell bags 300, prior to delivery of the cells to the cell collection bag 306.

Microcarriers, for example, CYTODEX® microcarrier beads (Pharmacia Biotech), can be also be added to cells in the cell collection bag 306 from a microcarrier container 320. From the microcarrier container 320, the microcarriers are delivered through conduit 304 to the cell collection bag 306 using a solution such as the diluent solutions listed above.

A suspension of cells and an agent taken from cell collection bag 306 through port 328 via and added at lateral ports 104 or 106 to the enclosure in the cell encapsulation device 10 (FIG. 1). Methods of removing cells from the cell collection bag 306 to cell encapsulation device 10 are described in detail in U.S. Pat. No. 5,643,794. In one method, cells are delivered to the encapsulation device by applying about 150 mm Hg pressure to the cell encapsulation device 10 with a pressure cuff.

The cell encapsulation device 10 can be gently rocked in order to facilitate dispersion of the cells in the enclosure. Air entering the enclosure can be used to help mix cells. However, air occupying more than 10–20% of the enclosure space is preferably purged.

Referring back to FIG. 1, wash buffer can be added directly to the enclosure through lateral ports 104 or 106. If desired, wash buffer is introduced first to the cell collection bag 306 and then added to the enclosure. Wash buffer may for some applications be added to the lumen of the hollow fibers via longitudinal inlet port 108. From the lumen it crosses the membranes of the hollow fibers into the enclosure containing the suspension of cells and back into the lumen, thereby dialyzing the agent to be removed.

Once inside the enclosure, the wash buffer and agent present in the suspension of cells passes across the membranes of the hollow fibers to the lumen, while the cells remain in the enclosure. The wash buffer containing the agent is then removed from the lumen through longitudinal outlet port 110 and conveyed to a waste bag. Alternatively, the wash buffer may be removed through one of the lateral ports 104 or 106 to which a barrier, e.g., a semipermeable membrane or filter, has been attached to prevent loss of cells.

Elimination of the agent can be monitored using an assay that detects the presence or absence of the agent. For example, removal of the cryoprotectant DMSO can be monitored by osmometry or with an HPLC analytical assay. Metabolic activity of the washed cells can be measured for porcine hepatocytes, for example, by measuring their ability to metabolize diazepam, glucose, or galactose.

The cell encapsulation device 10 can be connected to a bioprocessing system through a conduit connected to an external system. The external system can include components such as a plasma separation machine, a peristaltic pump, charcoal filters, an oxygenator/heat exchange unit, a reservoir bag for accommodating surges in plasma flow, and waste bags, all of which are discussed in greater detail in U.S. Pat. No. , 5,643,794. Before the cell encapsulation device 10 is connected to the system, the system is generally flushed with a suitable solution, e.g., saline or PBS.

It is noted that the above-described washing steps can take place either before or after the cell encapsulation device 10 is connected to the bioprocessing system. When washing takes place with the cell encapsulation device 10 connected to the bioprocessing system, the system is arranged so that the agent removed from the device in the wash buffer is diverted to a waste bag.

With the cryoprotectant separated from the cells, cell encapsulation device 10 is now ready for use for bioprocessing a fluid. For example, plasma can be introduced to the cell encapsulation device 10 by simply adapting the bioprocessing system to receive plasma from a plasma separation machine. Once the cell encapsulation device 10 is attached to the above-described system, plasma passes through the membrane to the hepatocytes, which metabolize toxins present in the plasma and proteins used to add other beneficial factors to the plasma. The processed plasma then returns to the lumen and exits the cell encapsulation device 10 through port 110, where it continues to circulate through the system.

In addition to being used in situ, the cell encapsulation device 10 can alternatively be transported and connected to a bioprocessing system at a second site. No transfer-associated loss or damage to the cells occurs because both the removal of the agent from the cells and the bioprocessing step are carried out with the cells in the encapsulation device 10.

Among other advantages, the suspension containing cells and cryoprotectant is added directly to the cell encapsulation device 10 without first removing the agent in one or more centrifugation and washing procedures.

The above-described embodiment describes the placement of cells in the extracapillary space of the cell encapsulation device. However, for some applications it may be desirable to place the suspension of cells in the lumen of the hollow fibers in the cell encapsulation device 10. In these situations the cells can be added through longitudinal inlet port 108 while the longitudinal outlet port 110 is closed. The agent can be removed from the suspension of cells in the lumen by passing a wash buffer from longitudinal inlet port 108 into the lumen, after which the buffer passes through the hollow fiber membrane to the extracapillary space of the cell encapsulation device 10, exiting the chamber through either or both of the lateral ports 104 or 106. Alternatively, the wash buffer can dialyze the suspension of cells in the lumen by entering through the lateral ports 104 (106) and pass from the extracapillary space into the lumen. The wash buffer, with the agent to be removed, then pass through the hollow fiber membrane and exit the cell encapsulation device 10 thorough another of the lateral ports 106 (104).

Another enclosure suitable for use in the methods of the invention is an enclosure that is defined in part by impermeable walls and in the remaining part by a membrane sheet which is permeable to the agent but not to the cells, thereby retaining the cells in the enclosure. A suspension of cells containing an agent is added through an input conduit to the enclosure. A wash buffer is then passed through the input conduit to the enclosure and transfers the agent through the membrane continuing through an output conduit. After the agent has been removed, a fluid can be provided through the input conduit to the cells in the enclosure, which can then bioprocess the fluid. The bioprocessed fluid is then removed through the outlet conduit.

The following specific examples are to be construed as merely illustrative, and not limitive of the remainder of the disclosure. All patents, patent applications, and publications cited herein are hereby incorporated by reference.

EXAMPLE 1

Use of a cell encapsulation device to remove DMSO from a suspension of porcine hepatocytes The ability of a membrane to remove an agent from a suspension of cells was examined by using a cell encapsulation device (BAL-2000 Membrane Cartridge, Circe Biomedical, Lexington, Mass.) as shown in FIG. 1 and FIGS. 2A–2C to remove DMSO from a thawed suspension of porcine hepatocytes. The cell encapsulation device included hollow fibers made of a polysulfone, 0.15-$\mu$m pore size hollow fiber membrane (Circe Biomedical, Lexington, Mass.).

To introduce cells into the enclosure of the cell encapsulation device, six CRYOCYTE™ bags of a frozen suspension of porcine hepatocytes in DMSO were removed, two at a time, from storage in liquid nitrogen and thawed for two minutes in a 42° C. water bath. The thawed cells were then attached to a 1 liter bag of PBS which was maintained at room temperature or warmer and at a pH of 7.2–7.4. Some PBS buffer was allowed to drain into the cell bags, after which the saline bag was clamped. A clear path was created from the cell bags to the enclosure in the cell encapsulation device, which had been pre-rinsed with saline and PBS. The contents of both cell bags were then allowed to drain into the enclosure. Excess liquid was allowed to leave the device, after which the device was flushed with 500 ml PBS.

The cell encapsulation device was gently rocked to mix the cells. If air occupied more than 10–20% of the available shell-side space of the device, the excess air was purged. PBS continued to be drained through the device until a total of 2.5 liters of PBS had been used.

The cell encapsulation device containing the cells and microcarriers was then attached to a HEPATASSIST® 2000 circuit (Circe Biomedical, Lexington, Mass.) constructed essentially as described in U.S. Pat. No. 5,643,974. Prior to the attachment of the cell encapsulation device, the circuit was primed with 3 liters of saline, followed by 1 liter of calf serum. After the cell encapsulation device was attached, fluid was allowed to flow in the circuit through the device.

For cells from which DMSO was removed using conventional centrifugation, the thawing procedure described as above was followed, after which cells were centrifuged at 600 RPM for 1.5 minutes in a Cobe 2991 Cell Processor (Cobe Laboratories, Arvada, Colo.). The supernatant was withdrawn at a rate of 200 mL/min. Following centrifugation, pelleted cells were washed twice with DMEM and twice with cold saline.

The ability of a cell encapsulation device to remove DMSO from a suspension of cells was compared to removal of DMSO using conventional centrifugation by measuring the change in osmolality of the suspensions as increasing volume of wash solutions were added. The osmolality unexpectedly decreased at a comparable rate in the two procedures, demonstrating that washing the cells with the membrane was as effective in removing cryoprotectant as conventional centrifugation and following introduction of comparable volumes of wash media.

EXAMPLE 2

Metabolic activity of a suspension of porcine hepatocytes following removal of DMSO with a cell encapsulation device The metabolic activity of porcine hepatocytes from which DMSO was removed using the cell encapsulation device was determined. For comparison, metabolic activity was also measured on hepatocytes from which DMSO had been removed using conventional centrifugation and washing procedures.

DMSO was removed from cells in the two different procedures was as described in Example 1, except that microcarriers were added to the cells. For cells washed with the cell encapsulation device, a one liter suspension of saline containing eight grams of CYTODEX® microcarrier beads (Pharmacia Biotech) was allowed to drain into a seeding bag via a sterile spike. The microcarriers and saline were then emptied from the seeding bag into the cell encapsulation device using a pressure infuser cuff and applying 150–300 mm Hg pressure. The cell encapsulation device was agitated throughout the procedure to keep the microcarriers suspended and to promote thorough mixing of cells and microcarriers in the enclosure. The gentle mixing also served to evenly distribute microcarriers and cells throughout the enclosure.

For cells in which DMSO was removed by centrifugation and washing, cells were collected in a seeding vessel as described in U.S. application Ser. No. 08/716,769. CYTODEX® microcarrier beads (Pharmacia Biotech), supplied in pre-hydrated form, and then introduced into the seeding vessel by gravity draining, after which the contents of the seeding vessel were introduced into a membrane bioreactor device which had been primed as described above.

Aliqouts of cells subjected to the two washing procedures were counted to determine the total cell number, and their metabolism was monitored for six hours by measuring oxygen, galactose and diazepam utilization, as well as glucose production.

The results are shown in Table I. The rates shown for glucose, galactose, and diazepam metabolism are average values from 60 minutes to 360 minutes for the whole device during the experiment. The rates of oxygen, diazepam, and galactose metabolism indicate consumption, while the rate for glucose indicates production. The data demonstrate that cells from which the DMSO was removed using the membrane-based method had higher metabolic rates for some indices of metabolic activity as compared to metabolic activities in cells from which DMSO was removed by conventional centrifugation and washing procedures.

TABLE I

| Metabolic | Method of removing DMSO* | |
|---|---|---|
| Rate | Membrane | Centrifugation |
| Oxygen ($\mu$g/min) | 665 | 619 |
| Glucose (mg/h) | 136 | 186 |
| Galactose (mg/h) | 107 | 95 |
| Diazepam ($\mu$g/h) | 1116 | 949 |

*$5.46 \times 10^9$ cells were used for both procedures.

EXAMPLE 3

Predilution of porcine hepatocytes prior to removal of DMSO with a membrane bioreactor device A thawed suspension of porcine hepatocytes containing DMSO was diluted prior to being added to the cell encapsulation device. After removal of DMSO, the metabolic activity of the cells was measured as described in Example 2. Metabolic activity in porcine hepatocytes from which DMSO had been removed using centrifugation and washing, also as described in Example 2, was examined as a control.

Six bags of porcine hepatocytes frozen in the presence of DMSO were thawed as described in Example 1, except that after thawing the cells were added to a sterile bottle instead of directly into the cell encapsulation device. 300 ml of PBS at 37° C. was next added to the bottle, along with 8 grams of CTYODEX™ microcarriers (Pharmacia Biotech) in a volume of 250 ml. The cell suspension was poured from the bottle to a seeding vessel. An inflation cuff, with 150 psi of applied pressure, was then used to transfer the cells and microcarriers from the seeding vessel to the cell encapsulation device. The device was rinsed with 2 liters of warm PBS, and the cell encapsulation device was connected to a HEPATASSIST® 2000 circuit (Circe Biomedical, Lexington, Mass.). Metabolic activity was measured as described in Example 2.

Table II reveals that hepatocyte metabolic activity was higher in cells subjected to DMSO-removal using the dilution and membrane washing method compared to cells from which DMSO had been removed using conventional centrifugation and washing. Thus, dilution followed by flushing using the membrane bioreactor device is also an effective method of removing DMSO from thawed suspensions of porcine hepatocytes.

TABLE II

| Metabolic | Method of removing DMSO* | |
|---|---|---|
| Rate | Membrane | Centrifugation |
| Oxygen ($\mu$g/min) | 1009 | 732 |
| Glucose (mg/h) | 277 | 235 |
| Galactose (mg/h) | 144 | 103 |
| Diazepam ($\mu$g/h) | 3335 | 3096 |

*For the "Membrane" procedure, $4.43 \times 10^9$ cells were used. $6.79 \times 10^9$ cells were used in the "Centrifugation" procedure. Data shown are normalized to rates for $6.79 \times 10^9$ cells.

EXAMPLE 4
Comparison of One-Step and Two-Step Dilution

The dilution procedure described in Example 3 can be considered to be a "Two Step" dilution because diluted cells were first placed in a separate container and then added to the cell encapsulation device. In this example, the "Two Step" dilution method was compared to dilution and direct inoculation into the cell encapsulation device, i.e., "One Step" dilution.

To perform the "One Step" dilution, six bags of porcine hepatocytes frozen in the presence of DMSO were thawed and connected to a manifold. Two one liter bags of PBS were connected to the manifold, and an equal volume (100 ml) of PBS was added to each of the thawed bags of cells. The contents of each of the thawed bags were then immediately gravity fed into the cell encapsulation device. Microcarriers were then connected to the manifold circuit and gravity fed directly into the cell encapsulation device. An additional 2 liters of PBS was then rinsed through the cell encapsulation device to elute out the DMSO.

For cells subjected to the "Two Step" Dilution, cells were thawed, added to a container, and diluted with PBS as described in Example 3.

The effect of these two procedures on hepatocyte metabolism is shown in Table III. These results demonstrate that metabolic activity of porcine hepatocytes after using a membrane reactor to remove DMSO is comparable whether the cells are diluted directly in cell bags in one step, or added to a second container and then transferred to the cell encapsulation device.

TABLE III

| Metabolic Rate | Method of diluting cells* | |
|---|---|---|
| | One-Step | Two-Step |
| Oxygen ($\mu$g/min) | 809 | 688 |
| Glucose (mg/h) | 156 | 121 |
| Galactose (mg/h) | 102 | 101 |
| Diazepam ($\mu$g/h) | 4610 | 4060 |

*For each procedure, 7.86 × 10⁹ cells were used.

Other Embodiments

From the above description, one skilled in the art can easily ascertain the essential characteristics of the present invention, and without departing from the spirit and scope thereof, can make various changes and modifications of the invention to adapt it to various usages and conditions. For example, the membrane can be in the form of a flat sheet, in a plate-and-frame configuration, or spiral-wound. In addition, cells from which agents have been removed using membranes can also be used in other bioprocessing applications, such as bioremediation.

Without further elaboration, it is believed that one skilled in the art can, based on the description herein, utilize the present invention to its fullest extent. Other embodiments are also within the claims.

What is claimed is:

1. A method for bioprocessing a fluid comprising:
   adding a suspension containing cells and an undesirable agent to an enclosure, the enclosure defined in part by a semipermeable membrane which is permeable to the agent but not to the cells;
   passing a buffer into the enclosure until the agent has been removed from the suspension while the cells remain in the enclosure; and
   subsequently introducing a fluid into the enclosure for bioprocessing by the cells in the enclosure.

2. The method of claim 1, wherein the enclosure is defined in part by the outside surfaces of a multiplicity of bundled hollow fibers comprising the semipermeable membrane; and the buffer is passed into the enclosure and subsequently removed through the semipermeable membrane of the hollow fibers.

3. The method of claim 2, wherein the cells are mammalian cells.

4. The method of claim 3, wherein the fluid is plasma or blood.

5. The method of claim 4, wherein the agent is a cryoprotectant.

6. The method of claim 5, wherein the suspension of cells contains a biomatrix for attachment of cells thereto.

7. The method of claim 3, wherein the agent is a cryoprotectant.

8. The method of claim 7, wherein the suspension contains a biomatrix for attachment of cells thereto.

9. The method of claim 3, wherein the suspension contains a biomatrix for attachment of cells thereto.

10. The method of claim 2, wherein the fluid is plasma or blood.

11. The method of claim 2, wherein the agent is a cryoprotectant.

12. The method of claim 1, wherein the enclosure is defined in part by the inside surfaces of a multiplicity of bundled hollow fibers comprising the semipermeable membrane; and the buffer is passed into the enclosure and subsequently removed through the semipermeable membrane of the hollow fibers.

13. The method of claim 1, wherein the cells are mammalian cells.

14. The method of claim 13, wherein the mammalian cells are hepatocytes.

15. The method of claim 1, wherein the fluid is plasma or blood.

16. The method of claim 1, wherein the agent is a cryoprotectant.

17. The method of claim 1, wherein the suspension contains a biomatrix for attachment of cells thereto.

18. A method for removing an undesirable agent from a suspension of cells comprising:
   adding the suspension to an enclosure defined in part by surfaces of a multiplicity of bundled hollow fibers which are made of a semipermeable membrane, said semipermeable membrane being permeable to the agent but not to the cells; and
   passing a buffer into the enclosure until the agent has been removed from the suspension through the semipermeable membrane, while the cells remain in the hollow fiber.

19. The method of claim 18, wherein said enclosure is defined in part by the outside surfaces of the bundled hollow fibers.

20. The method of claim 19, wherein the agent is a cryoprotectant.

21. The method of claim 18, wherein the cells are mammalian cells.

22. The method of claim 21, wherein the cells are hepatocytes.

23. The method of claim 22, wherein the agent is a cryoprotectant.

24. The method of claim 18, wherein the suspension contains a biomatrix for attachment of cells thereto.

* * * * *